United States Patent [19]

Ohuchi

[11] Patent Number: 5,417,099

[45] Date of Patent: May 23, 1995

[54] AIR-FUEL RATIO SENSOR TROUBLE DETECTING APPARATUS

[75] Inventor: Hirofumi Ohuchi, Hyogo, Japan

[73] Assignee: Mitsubishi Denki Kabushiki Kaisha, Tokyo, Japan

[21] Appl. No.: 251,177

[22] Filed: May 31, 1994

[30] Foreign Application Priority Data

Feb. 15, 1994 [JP] Japan .................................. 6-018738

[51] Int. Cl.$^6$ ...................... F02M 51/00; F02B 75/10; G01N 27/26
[52] U.S. Cl. ..................................... 73/23.32; 60/276; 60/285
[58] Field of Search .................. 73/23.32; 60/276, 285

[56] References Cited

U.S. PATENT DOCUMENTS

| | | | |
|---|---|---|---|
| 3,939,654 | 2/1976 | Creps | 60/276 |
| 4,278,060 | 7/1981 | Isobe et al. | 123/440 |
| 4,502,444 | 3/1985 | Rubbo et al. | 123/440 |
| 4,505,246 | 3/1985 | Nakajima et al. | 123/489 |
| 4,753,203 | 6/1988 | Yamada | 123/440 |
| 5,052,361 | 10/1991 | Ono et al. | 123/489 |
| 5,181,499 | 1/1993 | Kayanuma | 123/690 |
| 5,249,453 | 10/1993 | Usami et al. | 73/23.32 |

FOREIGN PATENT DOCUMENTS

| | | | |
|---|---|---|---|
| 3272452 | 12/1991 | Japan | 73/23.32 |
| 4050762 | 2/1992 | Japan | 73/23.32 |
| 4069567 | 3/1992 | Japan | 73/23.32 |
| 4204047 | 6/1992 | Japan | 73/23.32 |

Primary Examiner—Hezron E. Williams
Assistant Examiner—J. David Wiggins
Attorney, Agent, or Firm—Sughrue, Mion, Zinn, Macpeak & Seas

[57] ABSTRACT

An air-fuel ratio sensor malfunction detecting apparatus detects the output signal periods of a first or upstream air-fuel ratio sensor, and compares them with a predetermined value to judge the first sensor to be malfunctioning when the periods are larger than the predetermined value. The apparatus also compares the magnitudes of air-fuel ratio control quantities from a second or downstream air-fuel ratio sensor with a predetermined value to judge the first sensor to be malfunctioning when the air-fuel ratio control quantities are larger than the predetermined value.

16 Claims, 10 Drawing Sheets

TABLE 1

| TROUBLE MODE | | VALUE OF C2 | PERIOD T2 |
|---|---|---|---|
| RESPONSE TIME CHANGES (A) | | | |
| | TIME-LAGS ON RICH SIDE AND LEAN SIDE INCREASE | NO CHANGE (IN CASE OF Vc) | ELONGATED |
| | TIME-LAG ON LEAN SIDE INCREASES | DECREASE OF C2 (IN CASE OF Vb) | LITTLE CHANGE |
| | TIME-LAG ON RICH SIDE INCREASES | INCREASE OF C2 | LITTLE CHANGE |
| OUTPUT VOLTAGE VARIATION(B) | | | |
| | POSITIVE VOLTAGE OFFSET (2) | INCREASE OF C2 | LITTLE CHANGE |
| | NEGATIVE VOLTAGE OFFSET (2) | DECREASE OF C2 | LITTLE CHANGE |
| AIR-FUEL RATIO CHANGE POINT SHIFT(C) | | | |
| | COME TO LEAN (3) | INCREASE OF C2 | LITTLE CHANGE |
| | COME TO RICH (3) | DECREASE OF C2 | LITTLE CHANGE |

FIG. 4 (1)
(PRIOR ART)
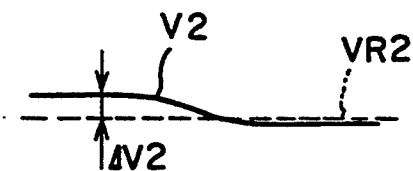
FIG. 4 (2)
(PRIOR ART)
FIG. 4 (3)
(PRIOR ART)
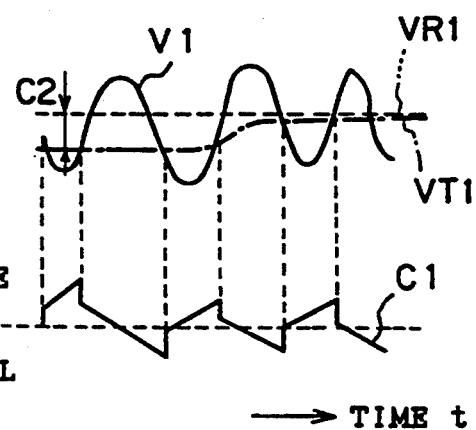

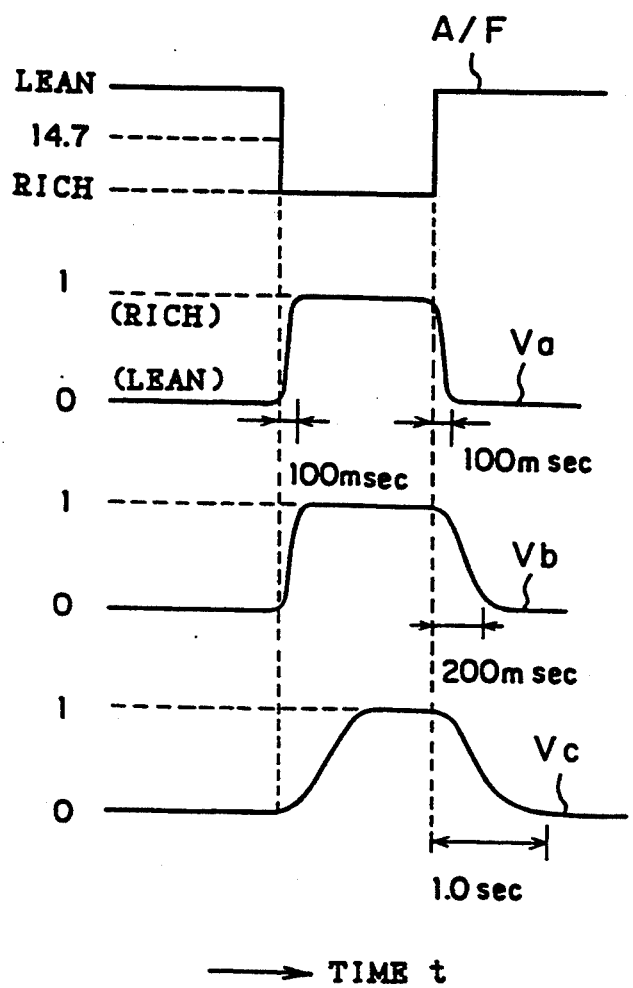

FIG. 6 (1)
(PRIOR ART)
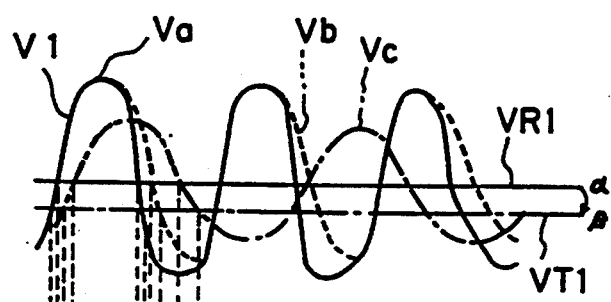
FIG. 6 (2)
(PRIOR ART)
FIG. 6 (3)
(PRIOR ART)
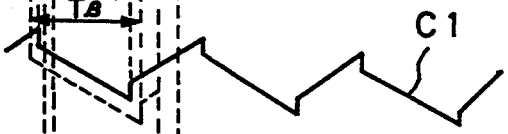
FIG. 6 (4)
(PRIOR ART)
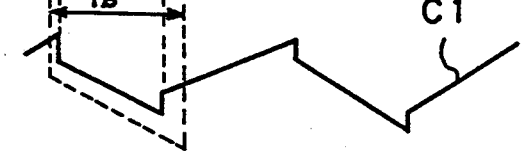
→ TIME t FIG. 9 (1)
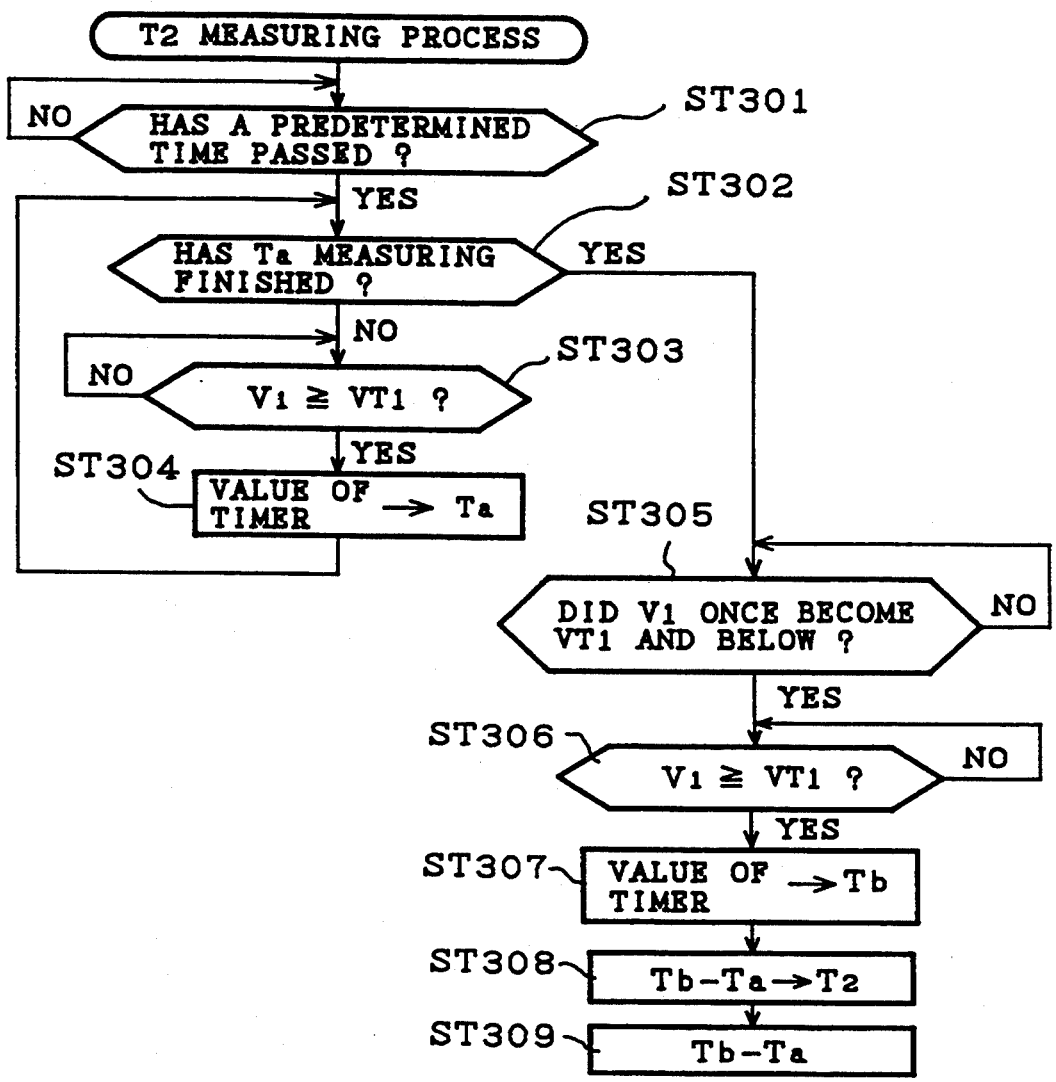
FIG. 9 (2)
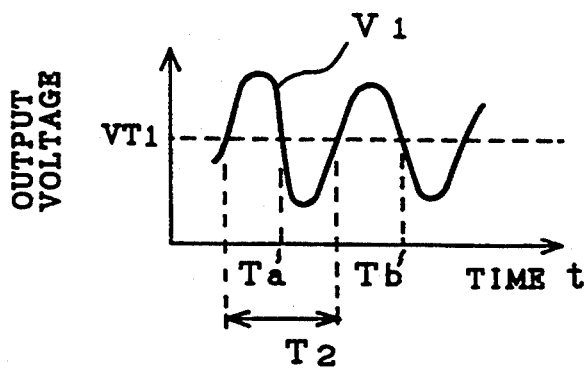

FIG. 10 (1)

TABLE 1

| TROUBLE MODE | | VALUE OF C2 | PERIOD T2 |
|---|---|---|---|
| RESPONSE TIME CHANGES (A) | | | |
| | TIME-LAGS ON RICH SIDE AND LEAN SIDE INCREASE | NO CHANGE (IN CASE OF Vc) | ELONGATED |
| | TIME-LAG ON LEAN SIDE INCREASES | DECREASE OF C2 (IN CASE OF Vb) | LITTLE CHANGE |
| | TIME-LAG ON RICH SIDE INCREASES | INCREASE OF C2 | LITTLE CHANGE |
| OUTPUT VOLTAGE VARIATION (B) | | | |
| | POSITIVE VOLTAGE OFFSET (FIG. 10 (2)) | INCREASE OF C2 | LITTLE CHANGE |
| | NEGATIVE VOLTAGE OFFSET (FIG. 10 (2)) | DECREASE OF C2 | LITTLE CHANGE |
| AIR-FUEL RATIO CHANGE POINT SHIFT (C) | | | |
| | COME TO LEAN (FIG. 10 (3)) | INCREASE OF C2 | LITTLE CHANGE |
| | COME TO RICH (FIG. 10 (3)) | DECREASE OF C2 | LITTLE CHANGE |

FIG. 10 (2)

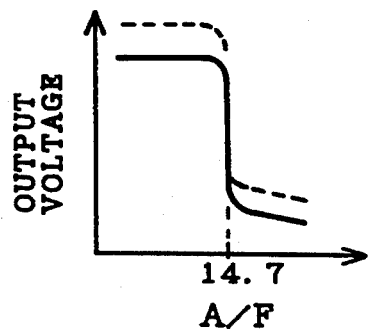

FIG. 10 (3)

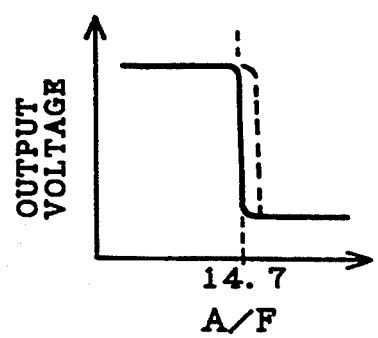

AIR-FUEL RATIO SENSOR TROUBLE DETECTING APPARATUS

BACKGROUND OF THE INVENTION

1. Field of the Invention

This invention in general relates to a trouble detecting apparatus of the air-fuel ratio sensors of internal combustion engines, and more particularly to an apparatus for detecting air-fuel ratio sensor trouble by the use of an air-fuel ratio control apparatus for internal combustion engines which executes the feedback control of air-fuel ratios on the basis of air-fuel ratio signals from two air-fuel ratio sensors respectively located at a front position and a rear position of a catalyzer in an exhaust pipe.

2. Description of the Prior Art

In general, the fuel injection quantities of internal combustion engines are controlled with feedback on the basis of signals from air-fuel ratio sensors ($O_2$ sensors and the like) located in exhaust pipes so that the air-fuel ratios of mixed air take optimum values (for example, about 14.7) according to the driving condition of the internal combustion engines.

Usually, the oxygen densities of exhaust gases decrease in the case where the air-fuel ratios of mixed gases are on a rich side when lower than 14.7, and the oxygen densities increase in the case where the air-fuel ratios of mixed gases are on a lean side being higher than 14.7, and consequently, the output signal voltage levels of the air-fuel ratio sensors vary between 0 [V] and 1 [V] according to the oxygen densities which in turn corresponds with the air-fuel ratios the typical value of which is 14.7. For example, if the air-fuel ratios are on the rich side, the voltage values of the output signals of the air-fuel ratio sensors (hereinafter referred to as "air-fuel ratio signals") increase according to the decrease of the oxygen densities.

However, in the case where a single air-fuel ratio sensor is located only on the upstream side of a catalyzer in an exhaust pipe, a high air-fuel ratio control precision is not obtained owing to the dispersion of the output characteristics (especially their operating points) of the air-fuel ratio sensors. Thus, apparatus has been proposed which is equipped with another air-fuel ratio sensor on the downstream side of the catalyzer, and which executes the feedback control on the basis of the air-fuel ratio signals on the downstream side of the catalyzer in addition to the feedback control on the basis of the air-fuel ratio signals on the upstream side of the catalyzer.

In this case, the air-fuel ratio sensor on the downstream side of the catalyzer senses the exhaust gases on the downstream side of the catalyzer which have averaged oxygen densities after catalytic reactions, and the degree of the deterioration of the air-fuel ratio sensor by the exhaust gases is reduced. Providing such a downstream side air-fuel ratio sensor makes the high precision feedback control of air-fuel ratios possible. That is to say, it can compensate for the dispersion of air-fuel ratio sensors, injectors (or fuel injecting valves) and the like, and it compensates for the changes with the passage of time of the output characteristics. Such a double air-fuel ratio sensor system is disclosed in, for example, U.S. Pat. No. 3,939,654.

FIG. 1 is a block diagram showing an example of an ordinary air-fuel ratio control apparatus for internal combustion engines which is equipped with air-fuel ratio sensors in a front position and in a rear position (or on the upstream side and on the downstream side) of a catalyzer.

In FIG. 1, reference numeral 1 designates an internal combustion engine (hereinafter referred to as "engine"); numeral 2 designates an intake pipe supplying mixed air to the engine 1; numeral 3 designates an air cleaner located at the intake aperture on the upstream side of the intake pipe 2; numeral 4 designates an intake manifold formed at the connection part of the downstream side end of the intake pipe 2 and the engine 1; and numeral 5 designates an injector, which is located on the upstream side of the intake pipe 2, for fuel injection.

Reference numeral 6 designates a semiconductor type pressure sensor sensing the pressure P in the intake manifold 4. The pressure sensor 6 measures the amount of air inhaled from the intake pipe 2 to the engine 1 through the intake manifold 4 as being proportional to the pressure P. Reference numeral 7 designates a throttle valve located on the downstream side of the injector 5 in the intake pipe 2.

Reference numeral 8 designates a throttle sensor for sensing the throttle opening degree $\phi$ of the throttle valve 7; numeral 9 designates an exhaust pipe leading the burned exhaust gases out from the engine 1; numeral 10 designates a catalyzer inserted into the exhaust pipe 9 and processing the exhaust gases by means of ternary processing; numeral 11 designates a first air-fuel ratio sensor located on the upstream side of the catalyzer 10; and numeral 12 designates a second air-fuel ratio sensor located on the downstream side of the catalyzer 10.

Reference numeral 13 designates an ignition coil composed of a step-up transformer, and numeral 14 designates an igniter composed of a power transistor breaking the electricity to the primary winding of the ignition coil 13. Reference numeral 15 designates an idle switch constructed with the throttle sensor 8 in a body. The idle switch 15 "turns on upon sensing the driving state of idling of the engine 1 when the throttle valve 7 is completely shut. Reference numeral 16 designates a thermistor type water temperature sensor sensing the cooling water temperature T of the engine 1; numeral 17 designates a battery as a power supply; and numeral 18 designates a key switch for starting the power-supply from the battery 17 and for ignition-driving; and numeral 19 designates a warning lamp activated activated when various malfunctions are sensed.

Reference numeral 20 designates an electrical control unit (hereinafter referred to as "ECU") controlling the drive of the injector 5 and the warning lamp 19 and the like in accordance with various driving states. The signals to be inputted to the ECU 20 as driving state designating signals are the throttle opening degrees $\phi$ from the throttle sensor 8, the pressure P in the intake manifold 4 from the pressure sensor 6, the cooling water temperature T from the water temperature sensor 16, idle signals D from the idle switch 15, rotation signals R based on the breaking of the electricity of the ignition coil 13, and air-fuel ratio signals V1 and V2 from each air-fuel ratio sensor 11 and 12 respectively.

The ECU 20 is operated by being fed from the battery 17 on closing the key switch 18, and the ECU 20 generates fuel injecting quantities J to the injector 5 in response to the air-fuel ratio signals V1, V2 and the drive states of the engine 1 to execute the feedback control of the air-fuel ratios, and further the ECU 20 generates signals E, which indicate the occurrences of malfunctions, to the warning lamp 19. The ignition signals for the igniter 14 may also be generated by the ECU 20.

FIG. 2 is a block diagram showing a concrete functional construction of the ECU 20. In FIG. 2, reference numeral 21 designates an input interface shaping the waveform of the rotation signal R to get interrupt signal INT; numeral 22 designates an input interface taking in the air-fuel ratio signals V1, V2, the pressure P, the water temperature T and the throttle opening degree $\phi$; numeral 23 designates an input interface taking in the idle signal D; numeral 24 designates an output interface outputting the malfunction signals E, the fuel injecting signals J and the like; numeral 25 designates a power supply circuit connected to the battery 17 through the key switch 18; and numeral 30 designates a microcomputer connected with the input interfaces 21–23, the output interface 24 and the power supply circuit 25.

The microcomputer 30 comprises a central processing unit (hereinafter referred to as "CPU") calculating air-fuel ratio feedback control quantities (hereinafter simply referred to as "air-fuel ratio control quantities") in accordance with the air-fuel ratio signal V1 and V2, a freely running counter 32 for measuring the rotational periods of the engine 1 on the basis of the rotation signal R through the input interface 21 or the interrupt signal INT, a timer 33 clocking for various controls, an analog-to-digital converter (hereinafter referred to as "A/D converter") 34 converting the analog signals through the input interface 22 (or the air-fuel ratio signals V1, V2, the pressure P, the water temperature T and the throttle opening degree $\phi$) into digital signals, an input port 35 taking in the idle signal D through the input interface 23, a random access memory (hereinafter referred to as "RAM") 36 used as a working memory of the CPU 31, a read-only memory (hereinafter referred to as "ROM") 37 memorizing the operating programs of the CPU 31 and the like, an output port 38 for outputting various control signals E and J through the output interface 24, and a common bus 39 connecting each element 32–38 to the CPU 31.

The CPU 31 reads the value of the counter 32 when an interrupt signal INT is inputted through the input interface 21, and the CPU 31 calculates the rotation period of the engine 1 from the deviation between this time value and the last time value of the counter 32 to store the calculated rotation period into the RAM 36.

The output interface 24 amplifies the control signals from the output port 38 to output them as the malfunction signals E and the fuel injecting signals J.

FIG. 3 is a functional block diagram schematically showing the air-fuel ratio feedback control arithmetic operation of the prior art microcomputer 30. In FIG. 3, reference numeral 41 designates a first PI controller executing a proportional-plus-integral control (hereinafter referred to as "PI control") of the air-fuel ratio signal V1 from the first air-fuel ratio sensor 11; and numeral 42 designates a second PI controller executing a PI control of the air-fuel ratio signal V2 from the second air-fuel ratio sensor 12.

Each PI controller 41 and 42 constitutes operation means for operating each air-fuel ratio control quantity C1 and C2 on the basis of each air-fuel ratio signal V1 and V2. The second air-fuel ratio controlling quantity C2 acts as a compensating quantity to the first air-fuel ratio control quantity C1. Furthermore, the first air-fuel ratio control quantity C1 corresponds to an air-fuel ratio compensating quantity, whereby the final fuel injecting signal J to the injector 5 is controlled with the feedback of the first air-fuel ratio control quantity C1, and the second air-fuel ratio signal V2 is made to accord with a second target value VR2.

VR1 and VR2 designate respectively first and second target values for air-fuel ratio control, which are predetermined for each air-fuel ratio signal V1 and V2. Each of the target values VR1, VR2 is set to a voltage value approximately corresponding to the optimum air-fuel ratio 14.7, but the second target value VR2 may be set at a voltage value a little higher than the target value VR1 (on the rich side or in accordance with the air-fuel ratio smaller than 14.7).

FR designates, a basic fuel quantity calculated from the pressure P corresponding to the inhaled air quantity, CF designates a fuel compensating quantity corresponding to the acceleration or the deceleration state of the engine 1 which is based on the water temperature T and the throttle opening degree $\phi$, KF designates an injection time compensating coefficient of the injector 5 to a target fuel quantity, and Q designates an inoperative time compensating quantity.

Reference numeral 43 designates a subtracter outputting a deviation $\Delta V2$ between the second target value VR2 and the air-fuel ratio signal V2 to input the obtained deviation $\Delta V2$ into the second PI controller 42, numeral 44 designates an adder adding the second air-fuel ratio control quantity C2 to the first target value VR1 to obtain a compensated target value VT1, and numeral 45 designates a subtracter obtaining a deviation $\Delta V1$ between the compensated target value VT1 and the air-fuel ratio signal V1 to input the deviation $\Delta V1$ into the first PI controller 41.

The adder 44 constitutes a compensating means for compensating the air-fuel ratio control quantity C1 calculated by the first PI controller 41.

Reference numeral 46 designates a multiplier multiplying the air-fuel ratio control quantity C1 from the first PI controller 41 by the basic fuel quantity FR to generate a target fuel quantity F1, numeral 47 designates a multiplier multiplying the target fuel quantity F1 by the fuel compensating quantity CF to generate a compensated fuel quantity F, numeral 48 designates a multiplier multiplying the compensated fuel quantity F by the injection time compensating coefficient KF to generate an activation time G of the injector 5, and numeral 49 designates an adder adding the inoperative time compensating quantity Q to the driving time G to generate the final fuel injecting signal J. These multipliers 46–48 and adder 49 constitute control quantity converting means for converting the air-fuel ratio control quantity C1 into the fuel injecting signal J.

Next, the concrete operation of the prior art air-fuel ratio controlling apparatus for internal combustion engines will be described with reference to FIGS. 4(1)–4(3) as well as FIGS. 1–3.

At first, as shown in FIG. 3 and FIG. 4(1), the subtracter 43 compares the second air-fuel ratio signal V2 on the downstream side of the catalyzer 10 and the second target value VR2 to generate the deviation $\Delta V2$ (=VR2−V2); and the second PI controller 42 executes the PI control of the deviation $\Delta V2$ to calculate the air-fuel ratio controlling quantity C2.

On the other hand, as shown in FIG. 3 and FIG. 4(2), the adder 44 adds the air-fuel ratio control quantity C2 or the compensating quantity to the first target value VR1 to generate the compensated target value VT1 (=VR1+C2) for the first air-fuel ratio sensor 11. Besides, the subtracter 45 compares the first air-fuel ratio signal V1 on the upstream side of the catalyzer 10 and the compensated target value VT1 to generate the deviation $\Delta V1$ ($=VT1-V1$); and the first PI controller 41, as shown in FIG. 4(3), executes the PI control of the deviation $\Delta V1$ to calculate the air-fuel ratio control quantity C1 for feedback.

Thus, the air-fuel ratio control quantity C1 on the basis of the first air-fuel ratio control signal V1 is compensated by the second air-fuel ratio control quantity C2 resulting in the final air-fuel ratio control quantity.

Next, the inhaled air quantity is sensed on the basis of the pressure P from the pressure sensor 6, and the basic fuel quantity FR is calculated from the inhaled air quantity. Then, the multiplier 46 multiplies the air-fuel ratio control quantity C1 by the basic fuel quantity FR to obtain the target fuel quantity F1.

Successively, the compensating quantity corresponding to the warming-up state of the engine i is calculated on the basis of the water temperature T from the water temperature sensor 16, and the acceleration or the deceleration state of the engine 1 which is based on the compensating quantity and the throttle opening degree $\phi$ from the throttle sensor 8 is sensed. Then, the fuel compensating quantity CF is calculated on the basis of the compensating quantity corresponding to the acceleration or the deceleration state and the like. Thus, the multiplier 47 multiplies the target fuel quantity F1 by the fuel compensating quantity CF to obtain the compensated fuel quantity F corresponding to the final fuel injection quantity.

Moreover, the multiplier 48 multiplies the compensated fuel quantity F by the injecting time compensating coefficient KF to obtain the driving time G of the injector 5, and the adder 49 adds the useless time compensating quantity Q to the driving time G to obtain the final fuel injecting signal J for the injector 5.

As described above, the air-fuel ratio feedback control is executed so that the air-fuel ratio signal V2 on the downstream side of the catalyzer 10 becomes the second target value VR2 by compensating the target value VR1 for the first air-fuel ratio sensor 11 using the air-fuel signal V2 from the second air-fuel sensor 12.

That is to say, if the air-fuel ratio signal V2 on the downstream side of the catalyzer 10 is shown to be on the lean side (where its air-fuel ratio is larger than 14.7), the fuel injecting signal J is set to be longer, and the air-fuel ratio is controlled to shift to the rich side. Also, if the air-fuel ratio signal V2 on the downstream side of the catalyzer 10 is shown to be on the rich side (where its air-fuel ratio is smaller than 14.7), the fuel injecting signal J is set to be shorter, and the air-fuel ratio is controlled to shift to the lean side. This situation will be described on the basis of the FIGS. 4(1)-(4(3) as follows. For example, if the signal V2 is on the rich side, the deviation $\Delta V2$, which is the result of the operation of subtracting the air-fuel ratio signal V2 from the second target value VR2, becomes positive. Then, the air-fuel ratio control quantity C1 is changed by introducing the compensated target value VT1, which is the result of the operation of subtracting the above-mentioned deviation $\Delta V2$ from the target value VR1 of the first air-fuel ratio sensor 11, and by making the time judged to be in the rich state be elongated. Thus, the fuel injection quantity is made to be decreased.

However, each air-fuel ratio sensor 11 and 12 has dispersion in its output characteristic in spite of being made under the control of their characteristics. Furthermore, in particular, the sensing device of the first air-fuel ratio sensor 11 on the upstream side is exposed to intense heat owing to being located nearer to the engine I than the second air-fuel ratio sensor 12, and the device of the sensor 11 is directly exposed to harmful exhaust gas ingredients which are not catalyzed by the catalyzer 10 yet. Consequently, the deterioration of the sensing device apt to happen so that changes with the passage of time of its characteristic are caused by the deterioration. On the other hand, the second air-fuel ratio sensor 12 is exposed to the exhaust gases which are lower in temperature and comparatively cleaner than those to which the first air-fuel ratio sensor 11 is exposed, and the changes with the passage of time scarcely happen. Hereinafter, the problems due to the dispersion of the output characteristics of the first air-fuel ratio sensor 11 and the deterioration of the devices will be concretely described.

FIGS. 5(2) to 5(4) are wave form charts showing the output response characteristics of ordinary air-fuel ratio sensors in the case where their air-fuel ratios (or A/F), a typical wave form of which is shown in FIG. 5(1), are made to be changed compulsively. Reference mark Va, shown in FIG. 5(2), designates an air-fuel ratio signal of an air-fuel ratio sensor the characteristic of which is central among the other characteristics; and air-ratio signals of air-ratio sensors, the characteristic of one of which is dispersed from the central characteristic and the sensing device of the other of which deteriorates, are designated respectively by the reference marks Vb and Vc, which are shown in FIGS. 5(3) and 5(4) respectively.

as shown in FIGS. 5(1)-5(4), when the air-fuel ratio changes to the lean side or to the rich side, which is divided by the border of the target value 14.7, the air-fuel ratio signal Va of the air-fuel ratio sensor having the central characteristic responds behind about 100 milli-seconds; the air-fuel ratio signal Vb of the air-fuel ratio sensor, the response of which from the rich side to the lean side is late, responds behind about 200 milli-seconds; and the air-fuel ratio signal Vc of the air-fuel ratio sensor, both the responses of which from the rich side to the lean side and from the lean side to the rich side are late, responds behind the maximum 1.0 second.

FIGS. 6(1)-6(4) are wave form charts showing the air-fuel ratio feedback control operation in the case where the air-fuel ratio sensors having each output characteristic of the air-fuel ratio signals Va-Vc shown in FIGS. 5(2)-5(4) respectively are used as the first air-fuel ratio sensor 11.

Herein, the first target value VR1 for the first air-fuel ratio signal V1 is designated by $\alpha$, and the compensated target value VT1 is designated by $\beta$, then the case where the first target value VR1 is compensated from $\alpha$ to $\beta$ with the air-fuel ratio control quantity C2 based on the second air-fuel ratio signal V2 will be described. That is to say, the case will be described where the second air-fuel ratio signal V2 is on the richer side (or its voltage value is higher) than the second target value VR2, then where the air-fuel ratio is controlled by the feedback to the lean side by decreasing the compensated target value VT1 by adding the negative air-fuel ratio control quantity C2 to the first target value VR1.

In FIGS. 6(2)-6(4), reference marks $T\alpha$ and $T\beta$ designate times during which the air-fuel ratio signal V1 is judged to be on the rich side by comparing the air-fuel ratio signal V1 with the target values $\alpha$ and $\beta$ respectively; mark $T\alpha$ designates the rich-judged time in the case where the target value is set to be α; and mark Tβ designates the rich-judged time in the case where the target value is set to be β.

For example, the rich-judged time of the air-fuel ratio control quantity C1 based on the air-fuel ratio sensor 11 having the air-fuel ratio signal Va (or the central characteristic), as shown in FIG. 6(2), is compensated to Tβ longer than Tα, then the target value of the air-fuel ratio is changed to the decreasing side (or the lean side of the air-fuel ratio), as shown in FIG. 6(2), and consequently, the air-fuel ratio can be changed to be lean.

In the same manner, the rich-judged time using the air-fuel ratio sensor which outputs the air-fuel ratio signal Vb or Vc, as shown in FIG. 6(3) or 6(4) respectively, changes to Tβ longer than Tα by compensating the target value of the first air-fuel ratio signal V1 from α to β.

at this time, since the response times are different as shown in FIGS. 5(2)-5(4) owing to the dispersion of the output characteristics of the air-fuel ratio sensors 11 such as each air-fuel ratio signal Va—Vc, the change quantities (Tβ−Tα) of the rich-judged times differ according to the cases of each air-fuel ratio signal Va, the central characteristic, Vb and Vc, as shown in FIGS. 6(2)-6(4).

As described above, in the case where the output characteristics of the first air-fuel sensors differ, the change quantities of the rich-judged times Tα and Tβ differ in obedience to the change quantity (β−α) of the first target value VR1 in accordance with the second air-fuel ratio control quantity C2. Consequently, the change quantities of the air-fuel ratio control quantity C1 differ in obedience to the air-fuel ratio control quantity C2, which is the compensating quantity of the first target value VR1, and differ in accordance with the differences among the output characteristics and response times of the first air-fuel ratio sensors 11. That is to say, in the case where the air-fuel ratio sensor 11 which outputs the air-fuel ratio signal Va (being central characteristic) is used, the response time is comparatively fast, and consequently, the change quantity of the rich-judged time to the air-fuel ratio control quantity C2, being the compensating quantity of the first target value VR1, becomes small. As the result, appropriate air-fuel ratio control can be executed by changing the air-fuel ratio control quantity C2 as the compensating quantity of the first target value VR1.

Furthermore, in the case of the air-fuel ratio signal Vb, the response in changing from the lean side to the rich side is late, but the response in changing from the rich side to the lean side is comparatively fast, and consequently, appropriate air-fuel ratio control can be executed by compensating the first target value VR1 with the air-fuel ratio control quantity C2 through the air-fuel sensor 12.

Furthermore, in the case where the air-fuel sensor 11 outputting the air-fuel (signal Vc is used; since both the responses from the rich side to the lean side and from the lean side to the rich side are later than those of the air-fuel sensor, outputting the air-fuel signal Vb, the change quantity of the rich-judged time becomes larger, and Tβ becomes longer even if the air-fuel ratio control quantity C2 is changed, and consequently, the compensating quantity of the target value VR1 with the air-fuel ratio control quantity C2 becomes unacceptable for the 1.0 compensating quantity of the target value VR1 actually required, then the appropriate air-fuel ratio control cannot be executed. In particular, since the first air-fuel ratio sensor 11 on the upstream side of the catalyzer 10 is apt to deteriorate, the sensor 11 causes errors such that the changes of the : air-fuel ratio control quantity C1, and thus appropriate air-fuel ratio control, can not be attained.

Because the prior art air-fuel ratio control apparatus for internal combustion engines is constructed as mentioned above, it has a problem that it becomes difficult to execute appropriate air-fuel ratio control especially in the case where the air-fuel ratio signal is Vc owing to the dispersion of the first air-fuel ratio sensor and the changes of the characteristic due to the changes with the passage of time. Besides, in the case where the air-fuel ratio signal is Vb, appropriate air-fuel ratio control can be ensured, but it is better to detect the condition as being in trouble since the first air-fuel ratio sensor 11 itself is abnormal. On the other hand, it is desirable to judge the first air-fuel ratio sensor to be-out of order in the cases such that the magnitude of the air-fuel ratio signal V1, which is the output signal of the first air-fuel ratio sensor 11, changes, and that the change point of the first air-fuel ratio signal V1 shifts, whereas there is no description about such cases above.

SUMMARY OF THE INVENTION

In view of the foregoing, it is an object of the present invention to provide an air-fuel ratio sensor trouble detecting apparatus which can surely detect troubles of the first air-fuel ratio sensor to execute an appropriate air-fuel ratio control.

It is another object of the invention to provide an air-fuel ratio sensor trouble detecting apparatus which can prevent mis-detection and surely detect troubles.

It is a further object of the invention to provide an air-fuel sensor trouble detecting apparatus which can surely detect troubles without a waste.

According to the first aspect of the invention, for achieving the above-mentioned objects, there is provided an air-fuel ratio sensor trouble detecting apparatus comprising a period measuring means measuring a period of-crossing of a first air-fuel ratio signal over a compensated target value of a first air-fuel ratio control quantity, and a first judging means judging that the first air-fuel ratio sensor is in trouble in the case where the period measured by the period measuring means is larger than a predetermined value.

As stated above, the air-fuel sensor trouble detecting apparatus according to the first aspect of the invention measures the period of crossing of the first air-fuel ratio signal over the compensated target value of the first air-fuel ratio control quantity with the period measuring means, and judges that the first air-fuel ratio sensor is in trouble by the first judging means when the measured period is larger than the predetermined value, that is to say, when both the response times on the lean side and the rich side of the air-fuel ratio sensor become longer. Hereby, the trouble of the first air-fuel ratio sensor is surely detected and the appropriate control of air-fuel ratios can be surely executed.

According to the second aspect of the invention, there is provided an air-fuel ratio trouble detecting apparatus comprising a second judging means judging the first air-fuel ratio sensor to be in trouble when the second air-fuel ratio control quantity or the compensated quantity of the first air-fuel ratio control quantity is out of a predetermined range.

As stated above, the air-fuel ratio sensor trouble detecting apparatus according to the second aspect of the invention judges the first air-fuel ratio sensor to be in trouble when the second air-fuel ratio control quantity or the compensated target value is out of the predetermined range, that is to say, when a characteristic change on the lean side or the rich side happens. Hereby, the trouble of the first air-fuel ratio sensor is surely detected and the appropriate control of air-fuel ratios can be surely executed.

According to the third aspect of the invention, there is provided an air-fuel ratio sensor trouble detecting apparatus comprising a first trouble-judgement forbidding means forbidding the operation of the first and the second judging means in the case where the second air-fuel ratio control quantity or the compensated target value of the first air-fuel ratio control quantity does not keep a stable value.

As stated above, in the air-fuel ratio sensor trouble detecting apparatus according to the third aspect of the invention, the first trouble-judgement forbidding means forbids the operation of the first and the second judging means in the case where the second air-fuel ratio control quantity or the compensated target value of the first air-fuel ratio control quantity does not keep a stable value. Hereby, the trouble is surely detected without mis-detection because the judgement of the trouble is executed after the second air-fuel ratio control quantity is settled.

According to the fourth aspect of the invention, there is provided an air-fuel ratio sensor trouble detecting apparatus comprising a second trouble-judgement forbidding means forbidding the operation of the first and the second judging means in the case where the number of calculations of the second air-fuel ratio control quantity or the compensated target value of the first air-fuel ratio control quantity does not exceed a predetermined number.

As stated above, in the air-fuel ratio sensor trouble detecting means according to the fourth aspect of the invention, the second trouble judgement forbidding means forbids the operation of the first and the second judging means in the case where the number of calculations of the second air-fuel ratio control quantity or the compensated target value of the first air-fuel ratio control quantity does not exceed the predetermined number. This is based on the fact that the air-fuel ratio control quantity or the compensated target value can be considered to be stable if the number of calculations of the air-fuel ratio control quantity or the compensated target value does not exceed a predetermined number, thereby the sure trouble detection without a waste is enabled.

The above and further objects and novel features of the invention will more fully appear from the following detailed description when the same is read in connection with the accompanying drawings. It is to be expressly understood, however, that the drawings are for purpose of illustration only and are not intended as a definition of the limits of the invention.

BRIEF DESCRIPTION OF THE DRAWINGS

FIG. 4(1), FIG. 4(2) and FIG. 4(3) are wave form charts showing waveforms of air-fuel ratio signals and an air-fuel ratio control quantity of the air-fuel ratio control apparatus of FIG. 1.

FIG. 5(1), FIG. 5(2), FIG. 5(3) and FIG. 5(4) are wave form charts showing the output response characteristics of ordinary air-fuel ratio sensors in the case where their air-fuel ratios (or A/F) are made to be changed compulsively;

FIG. 6(1), FIG. 6(2), FIG. 6(3) and FIG. 6(4) are wave form charts showing the air-fuel ratio feedback control operation in the case where the air-fuel ratio sensors having each output characteristic of the air-fuel ratio signals shown in FIGS. 5(1)–5(4) respectively are used as the first air-fuel ratio sensor;

FIG. 9(1) and FIG. 9(2) are respectively a flow chart showing the measuring process of the periods of the output voltages of the first air-fuel ratio sensor among the trouble detecting processes of the first embodiment of the invention and a wave form chart showing an output voltage of the first air-fuel ratio sensor;

FIG. 10(1), FIG. 10(2) and FIG. 10(3) are respectively a table showing the states of the air-fuel ratio control quantity and the periods of the output voltages of the first air-fuel ratio output sensor in the case where the first air-fuel ratio sensor is in trouble and wave form charts showing waveforms of the output voltages of the air-fuel ratio sensor to air-fuel ratios;

DETAILED DESCRIPTION OF THE PREFERRED EMBODIMENTS

Preferred embodiments of the present invention will now be described in detail on reference to the accompanying drawings.

EMBODIMENT 1

Figure 1:
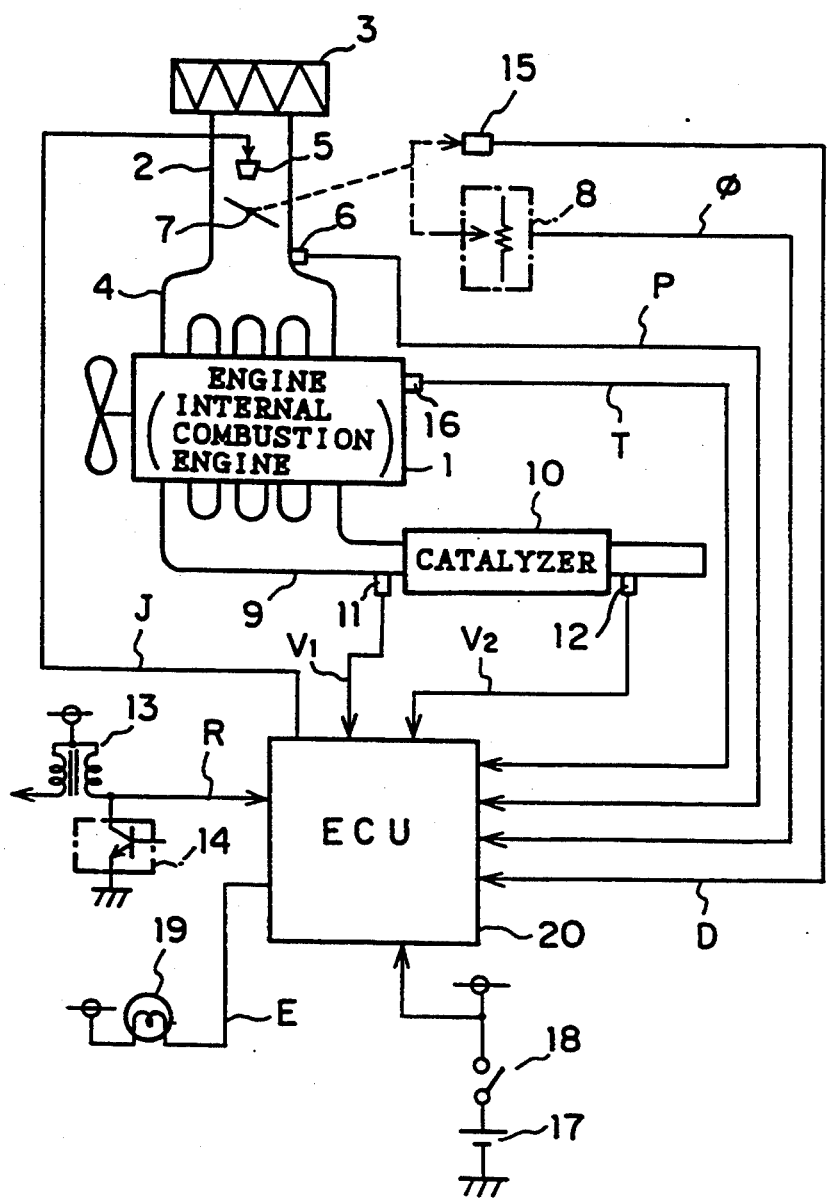
FIG. 1 is a block diagram showing an example of a prior art air-fuel ratio control apparatus for internal combustion engines.
Figure 2:
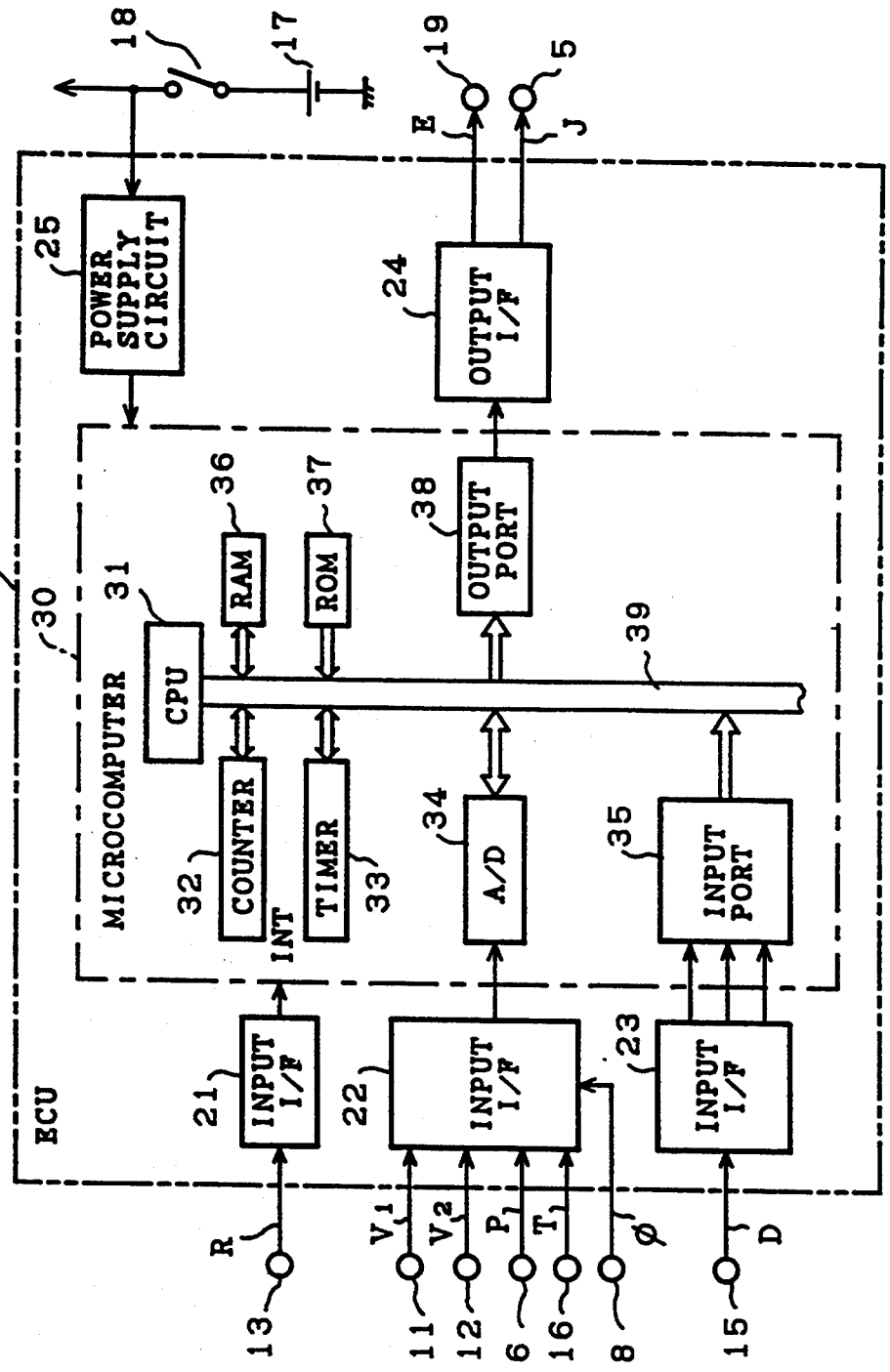
FIG. 2 is a block diagram showing a concrete functional construction of the ECU of the air-fuel ratio control apparatus for internal combustion engines of FIG. 1.
Figure 3:
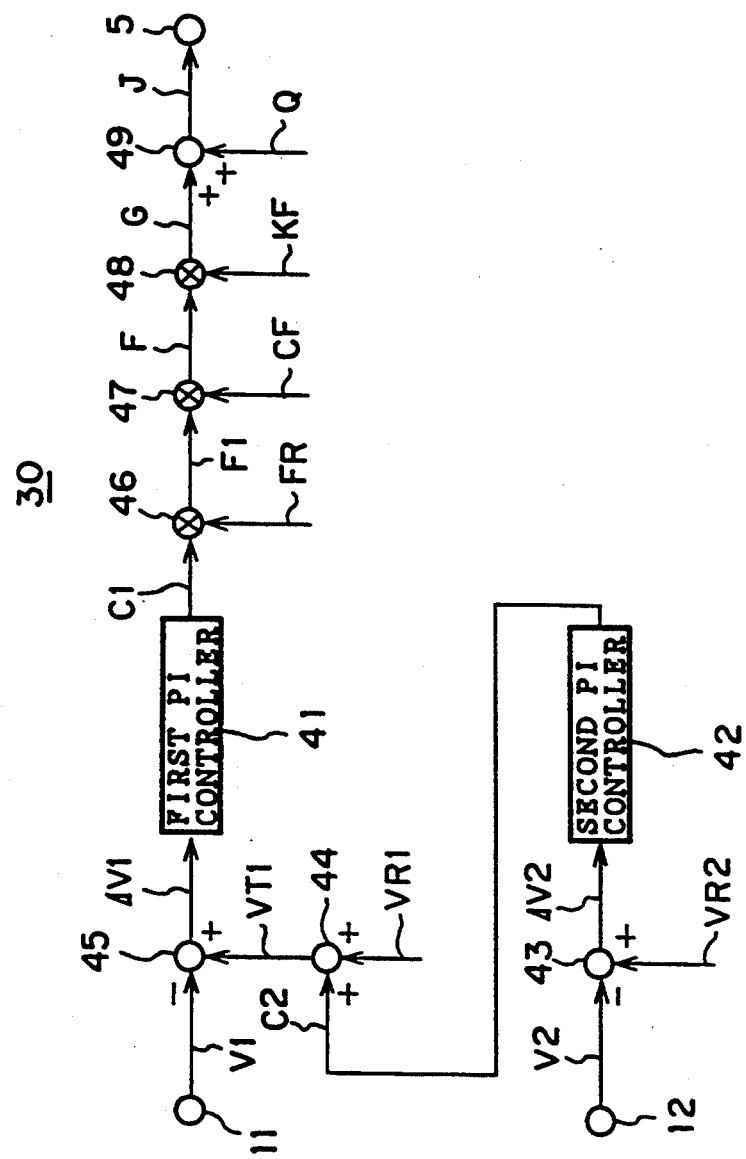
FIG. 3 is a functional block diagram schematically showing the air-fuel ratio feedback control arithmetic operation of a prior art microcomputer 30.

The construction of the hardware of the first embodiment of the present invention is the same as that of the prior art air-fuel ratio control apparatus for internal combustion engines shown in FIG. 1 and FIG. 2, and the description will be omitted thereof accordingly. Also, the arithmetic operation of the air-fuel ratio feedback control, to which the air-fuel ratio sensor trouble detecting apparatus of the invention is applied, is the same as the arithmetic operation of the prior art air-fuel ratio control apparatus for internal combustion engines shown in FIG. 3, and the description will be omitted thereof accordingly. That is to say, the an air-fuel ratio sensor trouble detecting apparatus of the invention is for detecting troubles of air-fuel ratio sensors of an air-fuel ratio control apparatus for internal engines equipped with two air-fuel ratio sensors 11, 12 at the front and the rear positions of the catalyzer 10; and the air-fuel ratio control apparatus typically has the construction shown in Figs. 1 and 2 and executes the arithmetic operation shown in FIG. 3.

Next, the principle of the operation of the embodiment will be described. The table 1 shown in FIG. 10(1) shows the states of the aforementioned second air-fuel ratio control quantity C2 and the period T2 at which interval the air-fuel ratio signal V1 from the first air-fuel ratio sensor 11 takes the same value as the air-fuel ratio control quantity C2 (refer to FIG. 9(2)) in the case where the changes of the characteristic of the first air-fuel ratio sensor 11 happen.

As shown in the table 1, in the case where the response times have changed owing to the trouble of the air-fuel sensor 11 (in case of (A) of the table 1) and further the response times on both of the rich side and the lean side have been elongated to enlarge time-lags like in the case of the air-fuel ratio signal Vc described in reference to FIG. 5(4) and FIG. 6(4), the time-lags on the rich side and on the lean side are offset by the compensation of the air-fuel ratio control quantity of the first air-fuel ratio sensor 11 by means of the second air-fuel ratio sensor 12; the value of the air-fuel ratio control quantity C2 is not changed, but the period T2 is elongated.

Besides, in the case where the response time on the lean side is elongated to enlarge the time-lag like in the case of the air-fuel ratio signal Vb described in FIG. 5(3) and FIG. 6(3), the value of the air-fuel ratio control quantity C2 is altered from the aforementioned target value α to the target value β by the air-fuel ratio signal V2 of the second air-fuel ratio sensor 12. That is to say, the value of the air-fuel ratio control quantity C2 decreases, and the change of the period T2 is small. Similarly, in the case where the response time on the rich side is elongated to enlarge the time-lag, the value of the air-fuel ratio control quantity C2 is compensated by the air-fuel ratio signal V2 of the air-fuel ratio sensor 12 and is altered in the opposite direction to the lean side, namely the value of the quantity C2 is altered in an increasing direction. In this case also, the change of period T2 is small.

Next, the description about the case of (B) of table 1, in which the magnitude of the air-fuel ratio signal V1 being the output voltage of the air-fuel ratio sensor 11 changes, will be done. As shown by the dotted line of FIG. 10(2), in the case where a positive offset voltage is generated to the normal state output voltage characteristic shown in the solid line, the output of the air-fuel ratio sensor 12 is on the lean side, and consequently, the value of the air-fuel ratio control quantity C2 is increased. Furthermore, since the response time does not change, the change of the period T2 is small. Similarly, in the case where negative offset voltages are generated, the value of the air-fuel ratio control quantity C2 decreases, and the change of the period T2 is small.

Furthermore, in the case of (C) of the table 1, in which the change point of the air-fuel ratio signal V1 shifts, as shown in FIG. 10(3), in the case where the change point of the air-fuel ratio signal V1 shifts to the lean side as shown by the dotted line to the normal state shown in the solid line, the value of the air-fuel ratio control quantity C2 increases and the period T2 hardly changes. Similarly, in the case where the change point of the air-fuel ratio signal V1 shifts to the rich side, the value of the air-fuel ratio control quantity C2 decreases and the period T2 hardly changes.

As described above, in the case where the air-fuel ratio sensor 11 is troubled due to some cause, some changes are caused in the air-fuel ratio control quantity C2 or the period T2 at which the air-fuel ratio signal V1 from the air-fuel ratio sensor 11 becomes equal to the air-fuel ratio control quantity C2. The trouble of the air-fuel ratio sensor 11 in some cases can be detected by detecting one of the quantity C2 and the period T2, whereas the perfect detection of the air-fuel ratio sensor 11 is enabled by detecting both of them.

This embodiment detects the trouble of the air-fuel ratio sensor 11 by detecting the value of the air-fuel ratio control quantity C2 and the aforementioned period T2 on the basis of the principle mentioned above. Hereinafter, the concrete operation of the embodiment will be described.

Figure 7:
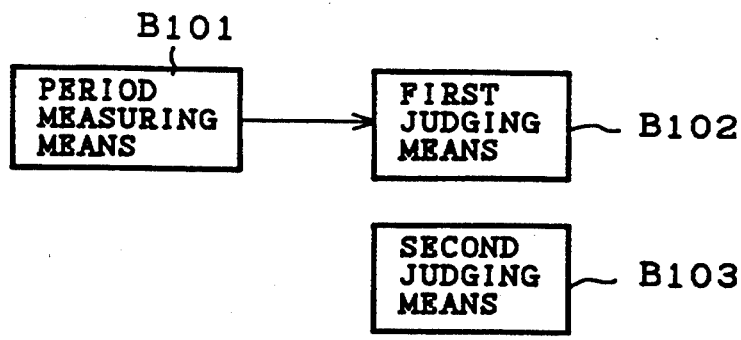
FIG. 7 is a functional block diagram showing a functional block of an air-fuel ratio sensor trouble detecting apparatus of a first embodiment of the present invention.

FIG. 7 is a functional block diagram showing the operation of the ECU 20 of the air-fuel ratio sensor trouble detecting apparatus of the embodiment. In FIG. 7, reference numeral B101 designates a period measuring means measuring the periods T2 at which interval the air-fuel ratio signal V1 crosses over a compensated target value of a first air-fuel ratio control quantity; numeral B102 designates a first judging means judging the first air-fuel ratio sensor 11 to be in trouble when the period T2 measured by the period measuring means B101 is not less than a predetermined value; and numeral B103 designates a second judging means judging the air-fuel ratio sensor 11 to be in trouble when the air-fuel ratio control quantity C2 is out of a predetermined range. Hereby, troubles of the air-fuel ratio sensor 11 can be detected by detecting aforementioned value of the air-fuel ratio control quantity C2 and the period T2.

Figure 8:
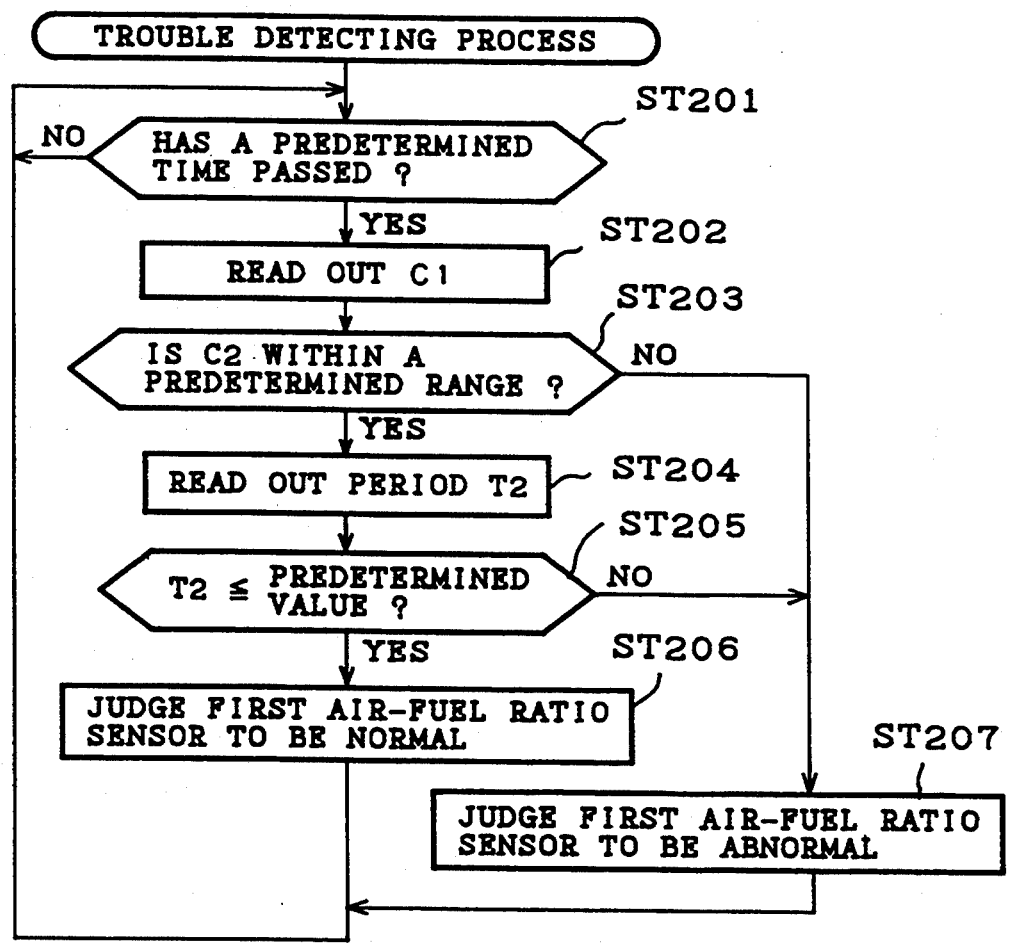
FIG. 8 is a flow chart showing the trouble detecting process of the first embodiment of the invention.

Next, the trouble detecting operation of the embodiment will be described on reference to the flow chart of FIG. 8. The microcomputer 30 of the ECU 20, at first, judges whether a predetermined time has passed or not after the last trouble detecting process (STEP ST201). If the predetermined time has not passed yet, the microcomputer 30 waits for the time to pass. That is to say, this trouble detecting process is executed after each predetermined time. If the predetermined time has passed, the microcomputer 30 reads out the air-fuel ratio control quantity C2 calculated by the PI controller 42 (STEP ST202), and judges whether the air-fuel ratio control quantity C2 read out is within a predetermined range in which appropriate air-fuel ratio control can be executed or not (STEP ST203). In the case where the air-fuel ratio control quantity C2 is out of the predetermined range, the microcomputer 30 moves to STEP ST207 and judges that the first air-fuel ratio sensor 11 is abnormal. In the case where the air-fuel ratio control quantity C2 is in the predetermined range, the microcomputer 30 moves to STEP ST 204 and reads out the period T2, then the microcomputer 30 judges whether the period T2 read out is more than a predetermined value, under which the air-fuel control can be executed, or not (STEP ST205). If the period T2 exceeds the predetermined value, the microcomputer 30 moves to STEP ST207 and judges that the first air-fuel sensor 11 is abnormal. Besides, if the period T2 does not exceed the predetermined value, the microcomputer 30 judges that the first air-fuel ratio sensor 11 is normal (STEP ST206). As mentioned above, the trouble detecting process is executed by judging the state of the air-fuel ratio sensor 11 on the basis of the magnitude of the value of the air-fuel ratio control quantity C2 and the magnitude of the period T2.

In this embodiment, the magnitude of the value of the air-fuel ratio control quantity C2 is judged, however it may be applicable to judge the magnitude of the compensated target value VT1 (=VR1 +C2) to the first air-fuel ratio sensor 11. Besides, in the embodiment, the predetermined range for judging the air-fuel ratio control quantity C2 and the predetermined value for judging the period T2 are made to be a fixed range and a fixed value respectively, however it may be applicable that the predetermined range and value are made to change according to the driving state of the internal combustion engine for surely executing the trouble detection of the air-fuel ratio sensor 11, because the appropriate range and value differ according to the driving state of the internal combustion engine. Furthermore, in the embodiment, aforementioned trouble detecting process is done every predetermined time with no connection with the driving state to of the internal combustion engine, however it may be applicable that the predetermined range and value for judging the air-fuel ratio control quantity C2 are previously fixed and then the process is executed every predetermined time only in the case where the internal combustion engine is in the driving state fitted to the aforementioned predetermined value and range. Furthermore, the judgement of the period T2, instead of being done by simply comparing the predetermined value like this embodiment, may be judged by whether the period T2 continuously exceeds the predetermined value for a predetermined time or not for eliminating the effects of the dispersion of the measured value of the period T2. Also, the period T2 may be averaged.

Next, the measurement processing operation of the period T2 will be described on reference to the flow chart of FIG. 9(1). At first, the microcomputer 30 judges whether the predetermined time has passed after the last measurement processing operation or not (STEP ST301), then the microcomputer 30 executes the measurement processing operation after the predetermined time has passed. This predetermined time is set to be much shorter than the period T2, then the measurement processing operation is executed every short predetermined time. After the predetermined time has passed, the microcomputer 30 judges, at first, whether the measurement of an initial time Ta for periods measuring or the first time when the air-fuel ratio signal V1 being the output voltage of the air-fuel ratio sensor 11 becomes equal to the air-fuel ratio control quantity C2 (refer to FIG. 9(2)) has finished or not (STEP ST302). If the measurement of the initial time Ta has not finished, the microcomputer 30 judges whether the air-fuel ratio signal V1 is not less than the air-fuel ratio control quantity C2 or not (STEP ST303). If the air-fuel ratio signal V1 is less than the air-fuel ratio control quantity C2, the microcomputer 30 waits until the signal V1 exceeds the quantity C2. And at the time when the air-fuel ratio signal V1 exceeds the air-fuel ratio control quantity C2, the microcomputer 30 memorizes the measured time value of the timer 33 at this time into the RAM 36 as the initial time Ta (STEP ST 304).

After the measurement of the initial time Ta has finished in such a way, the microcomputer 30, next, judges whether the air-fuel ratio signal V1 once took the compensated target value VT1 and below or not (STEP ST305). Because the period T2 cannot be judged if the air-fuel ratio signal V1 has not taken the compensated target value VT1 and below, the microcomputer 30 waits until the signal V1 takes the value VT1 and below. Then, at the time which the signal V1 takes the value VT1 and below, the microcomputer 30 moves to STEP ST306 and waits for the air-fuel ratio signal V1 to become VT1 or more. When the air-fuel ratio signal V1 becomes not less than the air-fuel ratio control quantity C2, the microcomputer 30 memorizes the measured time value of the timer 33 at that time into the RAM 36 as a finish time Tb (STEP ST307).

Successively, the microcomputer 30 calculates Tb Ta from the thus obtained initial time Ta and finish time Tb to obtain the period T2 (STEP ST308), after that the microcomputer 30 renews the initial time Ta by replacing the initial time Ta with the finish time Tb (STEP ST309). The periods T2 are measured by repeating the processes described above.

In this embodiment, the period T2 is obtained by measuring the change of the air-fuel ratio signal V1 from the lean side to the rich side, but the period T2 may be obtained by measuring the change from the rich side to the lean side. Moreover, the period T2 may be obtained by respectively measuring times when the air-fuel ratio signal V1 is on the rich side and on the lean side. Furthermore, the period T2 may be obtained by measuring the times at which the air-fuel ratio signal V1 crosses the compensated target value VT1 in the initial time. Besides, the compensated target value VT1 may have a hysteresis characteristic for removing the effects of the noise components of the air-fuel ratio signal V1.

EMBODIMENT 2

Figure 11:
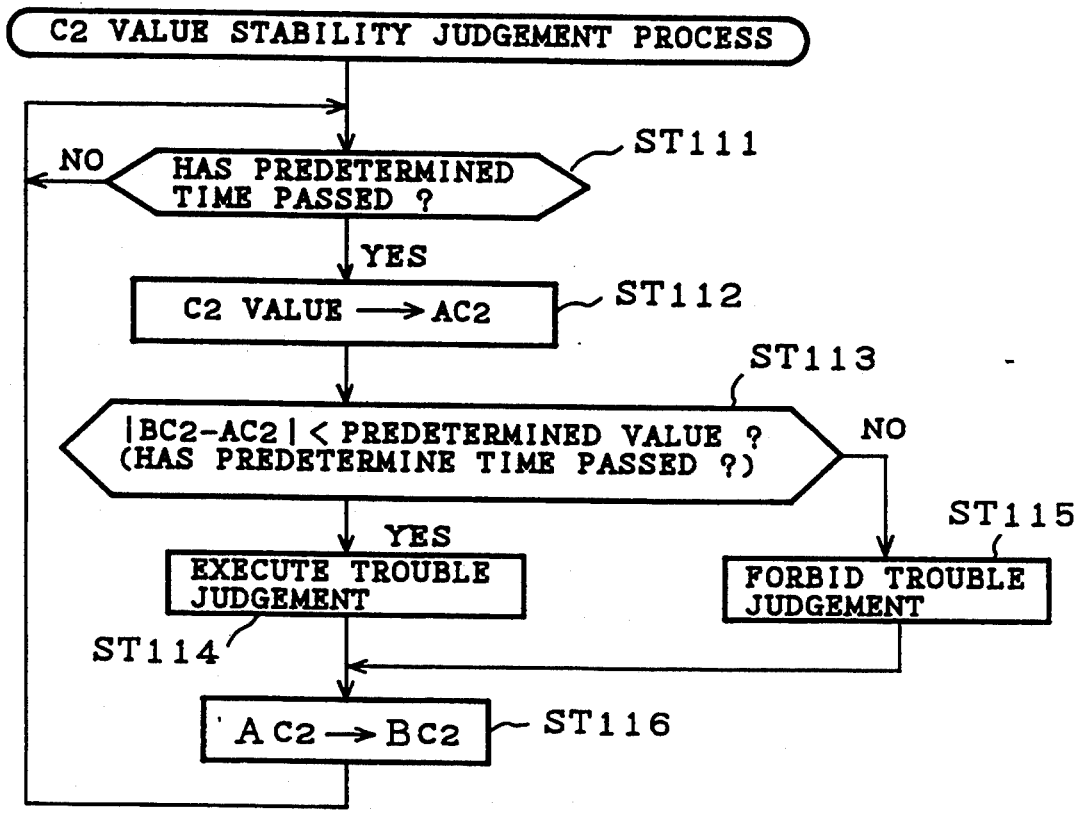
FIG. 11 is a flow chart showing a stability judging process of the air-fuel ratio control quantity of the air-fuel ratio sensor trouble detecting apparatus of the a second embodiment of the present invention.

Next, the embodiment 2, the second embodiment of the present invention, will be described. In this embodiment, too, the construction of its hardware is same as the construction of the prior art air-fuel ratio control apparatus for internal combustion engines shown in FIG. 1 and FIG. 2, and the arithmetic operation of its air-fuel ratio feedback control is also same as the arithmetic operation of the prior art air-fuel ratio control apparatus for internal combustion engines shown in FIG. 3, the description for them will be omitted accordingly. Furthermore, the trouble judging operation of the embodiment is same as the trouble judging operation of the first embodiment 1, the description also will be omitted thereof accordingly. This embodiment forbids the trouble or malfunction judging operation disclosed in the description of the embodiment 1 until the air-fuel ratio control quantity C2 takes stable values in accordance with situations of troubles of the first air-fuel ratio sensor 11 to prevent mis-judgements. Accordingly, the stability judging process of the air-fuel ratio control quantity C2 for preventing mis-judgement of this embodiment, next, will be described on reference to the flow chart of FIG. 11.

At first, the microcomputer 30 waits the passage of a predetermined time which is a time interval of executing this stability judging process (STEP ST111). After the predetermined time has passed, the microcomputer 30 memorizes the value of the air-fuel ratio control quantity C2 into the RAM 36 as a value AC2 (STEP ST112). In case of initially memorizing this value after the power supply 17 is thrown in, a value BC2 as a memorized value on the occasion of the last processing also is set to be a value equal to the value AC2 and initialized. Successively, the microcomputer 30 calculates the deviation between the value AC2 memorized in the RAM 36 and the value BC2 memorized at the last processing time, and judges whether this deviation |BC2−AC2| or the change of the air-fuel ratio control quantity C2 is smaller than a predetermined range or not (STEP ST113). If the deviation is smaller than the predetermined range, the microcomputer 30 moves to STEP ST114, and executes the trouble judging operation disclosed in the description of the first embodiment 1. If the deviation is not smaller than the predetermined value, the microcomputer 30 forbids the trouble judging operation, since the value of the air-fuel ratio control quantity C2 is-not stable (STEP ST115). After that, the microcomputer 30 renews the value AC2 by replacing the value AC2 with the value BC2 memorized in the RAM 36 at STEP ST116. Moreover, it may be applicable to add a process judging whether the state of the deviation |BC2−AC2| being smaller than the predetermined value has continued for a predetermined time or not to further ensure the stability judging process.

Figure 12:
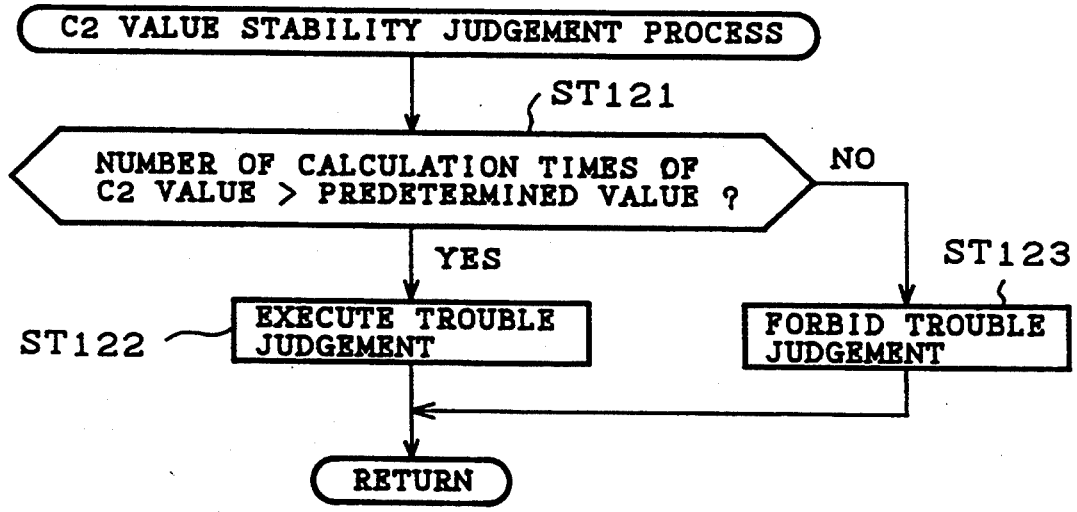
FIG. 12 is a flow chart showing a variation of the stability judging process of the embodiment of FIG. 11.

Next, a variation of the embodiment will be described. FIG. 12 is a flow chart showing the operation of a variation of the embodiment. In FIG. 12, the microcomputer 30 judges whether the number of calculation times Of the air-fuel ratio control quantity C2 exceeds a predetermined number of times or not (STEP ST121). If the number of the calculation times has exceeded the predetermined number of times, the microcomputer 30 executes the trouble judging operation disclosed in the description of the first embodiment 1 (STEP ST122). If the number of the calculation times does not exceeds the predetermined number of times, the microcomputer 30 forbids the trouble judging operation (STEP ST123). Thereby, the stability of the air-fuel ratio control quantity C2 can be judged. This is based on the fact that the air-fuel ratio control quantity C2 can be regarded to be stable, if the number of its calculation times exceeds a predetermined value in the case where, for example, the renewals of the PI controllers 41, 42 are executed every igniting input.

It will be appreciated from the foregoing description that, according to the first aspect of the invention, the air-fuel ratio sensor trouble detecting apparatus is constructed to measure the period of crossing of the first air-fuel ratio signal over the compensated target value of the first air-fuel ratio control quantity, and to judge that the first air-fuel ratio sensor is in trouble in the case where the measured period is larger than the predetermined value, and consequently, the air-fuel ratio sensor trouble detecting apparatus has such effects that the trouble of the first air-fuel ratio sensor can be surely detected especially in the case where the time-lags on the rich side and the lean side of the first air-fuel ratio sensor increase, and that the control of the air-fuel ratios can be executed appropriately.

Furthermore, according to the second aspect of the invention, the air-fuel ratio sensor trouble detecting apparatus is constructed to judge the first air-fuel ratio sensor to be in trouble when the second air-fuel ratio control quantity or the compensated quantity of the first air-fuel ratio control quantity is out of a predetermined range, and consequently, the air-fuel ratio sensor trouble detecting apparatus has an effect that the trouble of the first air-fuel ratio sensor can be surely detected especially in such cases that the first air-fuel ratio sensor increases its time-lag on the rich side or the lean side, that the output voltage changes, or that the change point of the air-fuel ratios shifts.

Furthermore, the air-fuel ratio sensor trouble detecting apparatus comprising both of the constructions of the first and the second aspects would be able to detect the trouble of the first air-fuel ratio sensor further completely.

Furthermore, according to the third aspect of the invention, the air-fuel ratio sensor trouble detecting apparatus is constructed to forbid the trouble detecting operation of the air-fuel ratio sensor, and consequently, the air-fuel ratio sensor control apparatus has such effects that mis-detections can be prevented and the trouble is surely detected.

Furthermore, according to the fourth aspect of the invention, the air-fuel ratio sensor trouble detecting apparatus is constructed to forbid the trouble judging operation of the air-fuel ratio sensor in the case where the number of the calculation times of, the second air-fuel ratio control quantity or the compensated target value of the first air-fuel ratio control quantity does not exceed a predetermined number of times, and consequently, the air-fuel ratio sensor trouble detecting means has such an effect that the sure trouble detection without waste judgements is enabled.

While preferred embodiments of the invention have been described using specific terms, such description is for illustrative purposes only, and it is to be understood that changes and variations may be made without departing from the spirit or scope of the following claims.

What is claimed is:

1. In an air-fuel ratio sensor malfunction detecting apparatus comprising a catalyzer for purifying exhaust gases, the catalyzer being inserted in an exhaust system of an internal combustion engine, a first air-fuel ratio sensor located on an upstream side of the catalyzer for sensing the density of a particular constituent of said exhaust gases as a first air-fuel ratio signal, a second air-fuel ratio sensor located on a downstream side of said catalyzer for sensing the density of said particular constituent of said exhaust gases as a second air-fuel ratio signal, and an electronic control unit (ECU) for generating a final air-fuel ratio control quantity on the basis of said first and second air-fuel ratio signals; said ECU including a first means for generating a first air-fuel ratio control quantity on the basis of said first air-fuel ratio signal, a second means for generating a second air-fuel ratio control quantity on the basis of said second air-fuel ratio signal, and a compensating means for compensating said first air-fuel ratio control quantity with said second air-fuel ratio control quantity to use as said final air-fuel ratio control quantity; the improvement comprising a time interval measuring means embodied in said ECU for measuring the time interval between successive crossings of a compensated target value of said first air-fuel ratio control quantity by said first air-fuel ratio signal, and a first judging means for judging said first air-fuel ratio sensor to be malfunctioning when a time interval measured by said measuring means is not less than a predetermined value.

2. The air-fuel ratio sensor malfunction detecting apparatus according to claim 1, wherein said measuring means executes time interval measurements after a predetermined time has elapsed.

3. The air-fuel ratio sensor malfunction detecting apparatus according to claim 1, wherein said predetermined value set in said first judging means changes according to driving states of said internal combustion engine.

4. The air-fuel ratio sensor malfunction detecting apparatus according to claim 1, wherein said first judging means judges said first air-fuel ratio sensor to be malfunctioning when said time interval is not less than said predetermined value for a predetermined time duration.

5. The air-fuel ratio sensor malfunction detecting apparatus according to claim 1, wherein said first judging means judges said first air-fuel ratio sensor to be malfunctioning when an average value of said time intervals is not less than said predetermined value.

6. The air-fuel ratio sensor malfunction detecting apparatus according to claim 1, further comprising a first malfunction judgement forbidding means for forbidding said judging operation of said first judging means when said second air-fuel ratio control quantity or said compensated target value of said first air-fuel ratio control quantity does not maintain a stable value.

7. The air-fuel ratio sensor malfunction detecting apparatus according to claim 6, wherein said first malfunction judging means compares said second air-fuel ratio control quantity or said compensated target value of said first air-fuel ratio control quantity at a certain time and each value after a predetermined time with a predetermined value to judge said each value to be stable when a deviation between said each value at times before and after said predetermined time does not exceed a predetermined value.

8. The air-fuel ratio sensor malfunction detecting apparatus according to claim 7, wherein said first malfunction judging means judges said each value to be stable when said deviation not exceeding said predetermined value lasts for a predetermined time.

9. The air-fuel ratio sensor malfunction detecting apparatus according to claim 1, further comprising a second malfunction judgement forbidding means for forbidding said judging operation of said first judging means when a number of calculating times of said second air-fuel ratio control quantity or said compensated target value of said first air-fuel ratio control quantity does not exceed a predetermined number.

10. In an air-fuel ratio sensor malfunction detecting apparatus comprising a catalyzer for purifying exhaust gases, the catalyzer being inserted in an exhaust system of an internal combustion engine, a first air-fuel ratio sensor located on an upstream side of the catalyzer for sensing the density of a particular constituent of said exhaust gases as a first air-fuel ratio signal, a second air-fuel ratio sensor located on a downstream side of said catalyzer for sensing the density of said particular constituent of said exhaust gases as a second air-fuel ratio signal, and an electronic control unit (ECU) for generating a final air-fuel ratio control quantity on the basis of said first and second air-fuel ratio signals; said ECU including a first means for generating a first air-fuel ratio control quantity on the basis of said first air-fuel ratio signal, a second means for generating a second air-fuel ratio control quantity on the basis of said second air-fuel ratio signal, and a compensating means for compensating said first air-fuel ratio control quantity with said second air-fuel ratio control quantity to use as said final air-fuel ratio control quantity; the improvement comprising a second judging means embodied in said ECU for judging said first air-fuel ratio sensor to be malfunctioning when said second air-fuel ratio control quantity or a compensated target value of said first air-fuel ratio control quantity is out of a predetermined range.

11. The air-fuel ratio sensor malfunction detecting apparatus according to claim 10, wherein said predetermined range set in said second judging means changes according to driving states of said internal combustion engine.

12. The air-fuel ratio sensor malfunction detecting apparatus according to claim 10, wherein said second judging measuring means executes malfunction judging on a periodic basis of once every predetermined time interval.

13. The air-fuel ratio sensor malfunction detecting apparatus according to claim 10, further comprising a first malfunction judgement forbidding means for forbidding said judging operation of said second judging means when said second air-fuel ratio control quantity or said compensated target value of said first air-fuel ratio control quantity does not maintain a stable value.

14. The air-fuel ratio sensor malfunction detecting apparatus according to claim 13, wherein said second malfunction judging means compares said second air-fuel ratio control quantity or said compensated target value of said first air-fuel ratio control quantity at a certain time and each valve after a predetermined time with a predetermined value to judge said each value to be stable when a deviation between said each value at times before and after said predetermined time does not exceed a predetermined value.

15. The air-fuel ratio sensor malfunction detecting apparatus according to claim 14, wherein said second malfunction judging means judges said each value to be stable when said deviation not exceeding said predetermined value lasts for a predetermined time.

16. The air-fuel ratio sensor malfunction detecting apparatus according to claim 10, further comprising a second malfunction judgement forbidding means for forbidding said judging operation of said first and second judging means when a number of calculating times of said second air-fuel ratio control quantity or said compensated target value of said first air-fuel ratio control quantity does not exceed a predetermined number.

* * * * *